(12) United States Patent
Müller et al.

(10) Patent No.: US 10,648,895 B2
(45) Date of Patent: May 12, 2020

(54) DEVICE AND METHOD FOR TESTING TABLETS

(71) Applicant: ERWEKA GmbH, Heusenstamm (DE)

(72) Inventors: Werner Georg Müller, Heusenstamm (DE); Levent Bozkurt, Heusenstamm (DE)

(73) Assignee: ERWEKA GMBH, Heusenstamm (DE)

( * ) Notice: Subject to any disclaimer, the term of this patent is extended or adjusted under 35 U.S.C. 154(b) by 250 days.

(21) Appl. No.: 15/756,896

(22) PCT Filed: Aug. 26, 2016

(86) PCT No.: PCT/EP2016/070229
§ 371 (c)(1),
(2) Date: Mar. 1, 2018

(87) PCT Pub. No.: WO2017/036980
PCT Pub. Date: Mar. 9, 2017

(65) Prior Publication Data
US 2018/0246023 A1    Aug. 30, 2018

(30) Foreign Application Priority Data

Sep. 1, 2015 (DE) .......................... 10 2015 114 600

(51) Int. Cl.
| | | |
|---|---|---|
| *G01N 3/40* | (2006.01) | |
| *G01N 33/15* | (2006.01) | |
| *G01B 5/08* | (2006.01) | |
| *G01N 33/00* | (2006.01) | |

(52) U.S. Cl.
CPC ................. *G01N 3/40* (2013.01); *G01B 5/08* (2013.01); *G01N 33/00* (2013.01); *G01N 33/15* (2013.01);
(Continued)

(58) Field of Classification Search
CPC ............ G01N 3/40; G01N 3/08; G01N 33/15; G01N 33/00; G01N 2203/0085;
(Continued)

(56) References Cited

U.S. PATENT DOCUMENTS

| | | | | |
|---|---|---|---|---|
| 4,884,463 A | * | 12/1989 | Kay ..................... | G01B 5/0002 73/865.8 |
| 6,257,079 B1 | * | 7/2001 | Mueller ................ | G01G 17/00 177/50 |

(Continued)

FOREIGN PATENT DOCUMENTS

| | | |
|---|---|---|
| DE | 197 33 436 C2 | 2/1999 |
| DE | 298 24 199 U1 | 10/2000 |

(Continued)

OTHER PUBLICATIONS

Translation of DE-202015101878-U1 (Year: 2015).*
International Search Report issued by the European Patent Office in International Application No. PCT/EP2016/070229.

*Primary Examiner* — Nathaniel T Woodward
(74) *Attorney, Agent, or Firm* — Troutman Sanders LLP

(57) ABSTRACT

A device and a method for testing tablets are disclosed. The device for testing tablets includes a test chamber, which has a crusher jaw and, lying opposite the latter, a counter-jaw. The device has a movable sheet metal strip, which is designed to position a tablet for testing. The longitudinal axis of the movable sheet metal strip is at an angle of less than 90° to the longitudinal axis of the direction of movement of the crusher jaw, and the direction of movement of the sheet metal strip corresponds to the longitudinal axis of the sheet metal strip.

16 Claims, 5 Drawing Sheets

(52) U.S. Cl.
CPC .............. *G01N 2033/0077* (2013.01); *G01N 2203/0019* (2013.01); *G01N 2203/0076* (2013.01); *G01N 2203/0085* (2013.01); *G01N 2203/0087* (2013.01); *G01N 2203/0206* (2013.01)

(58) Field of Classification Search
CPC ... G01N 2203/0076; G01N 2203/0077; G01N 2203/0206; G01N 2203/0087; G01N 2203/0019; G01B 5/08; B65G 47/24
USPC ............................................................ 73/78
See application file for complete search history.

(56) References Cited

U.S. PATENT DOCUMENTS

| | | | |
|---|---|---|---|
| 7,042,231 B2 * | 5/2006 | Trebbi | A61J 3/074 |
| | | | 324/639 |
| 7,364,103 B2 * | 4/2008 | Kraemer | G01N 3/04 |
| | | | 198/752.1 |
| 7,490,711 B2 * | 2/2009 | Schateikis | B65G 47/907 |
| | | | 198/431 |
| 9,835,533 B2 * | 12/2017 | Forcella | G01B 5/00 |

FOREIGN PATENT DOCUMENTS

| | | | |
|---|---|---|---|
| DE | 10 2004 059 976 A1 | 6/2006 | |
| DE | 10 2006 004 215 B4 | 8/2007 | |
| DE | 10 2013 015 582 B3 | 10/2014 | |
| DE | 2015 101878 U1 | 4/2015 | |
| DE | 202015101878 U1 * | 4/2015 | ............ G01N 33/15 |
| EP | 1 445 217 A2 | 8/2004 | |
| WO | WO 89/07083 A1 | 8/1989 | |
| WO | WO 2011/035818 A1 | 3/2011 | |
| WO | WO 2013/061223 A2 | 5/2013 | |
| WO | WO 2015/078600 A1 | 6/2015 | |

* cited by examiner

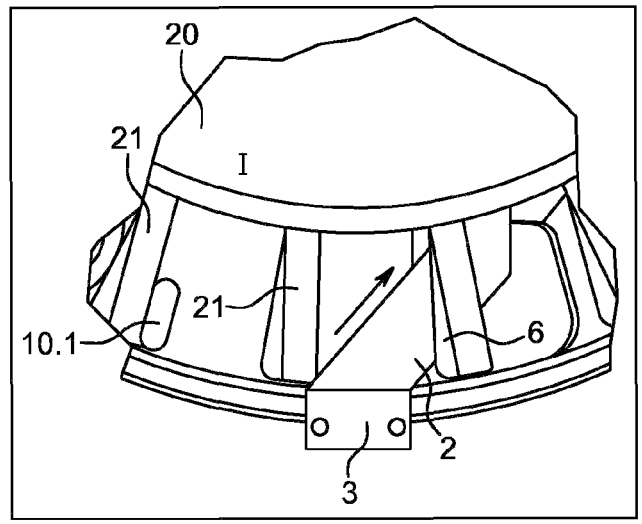
FIG. 3.1
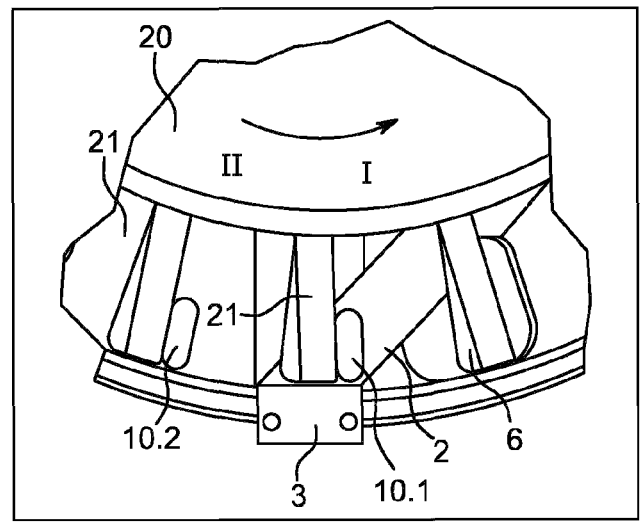
FIG. 3.2
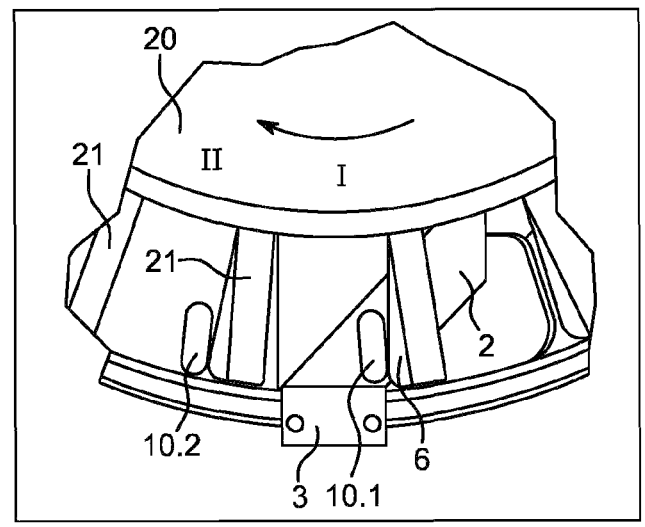
FIG. 3.3

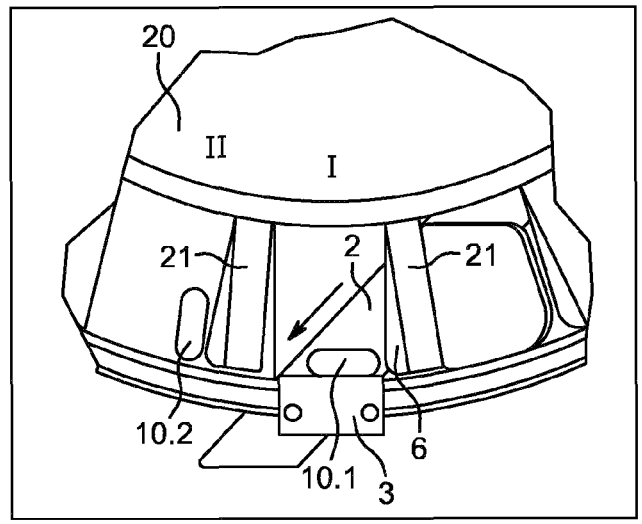
FIG. 3.4
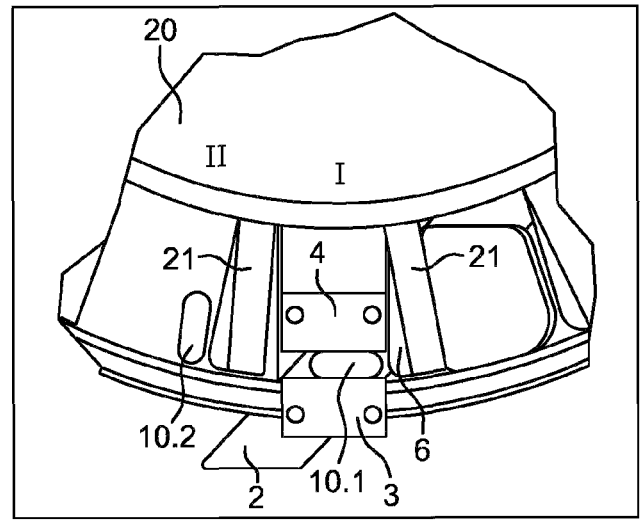
FIG. 3.5
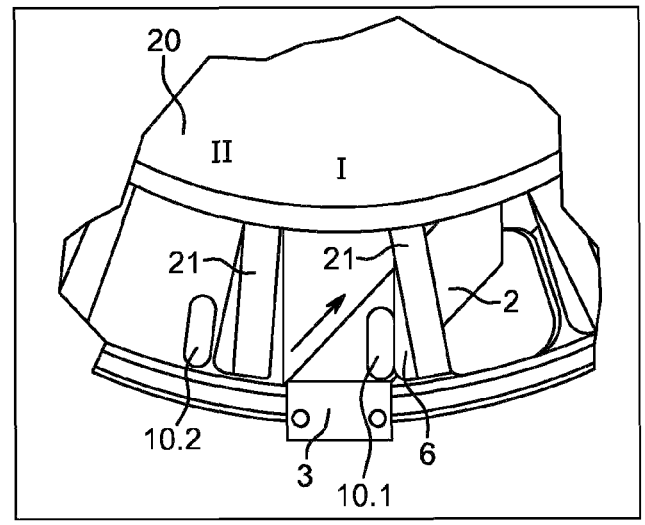
FIG. 3.6

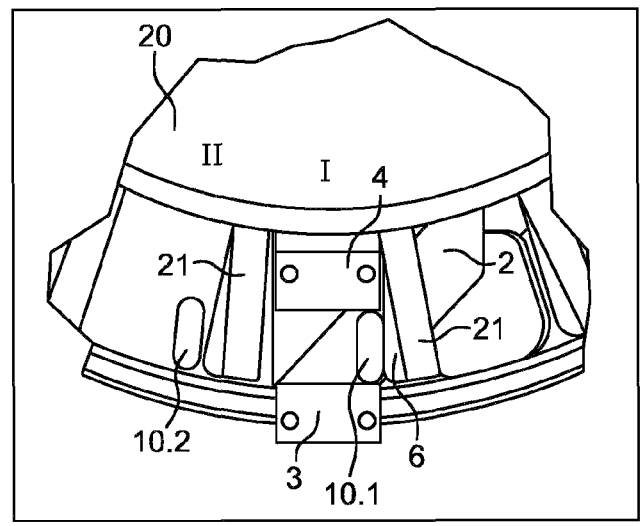
FIG. 3.7
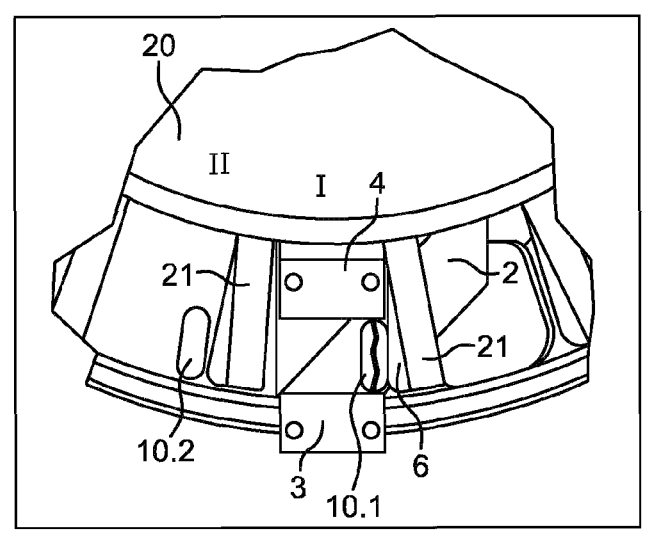
FIG. 3.8
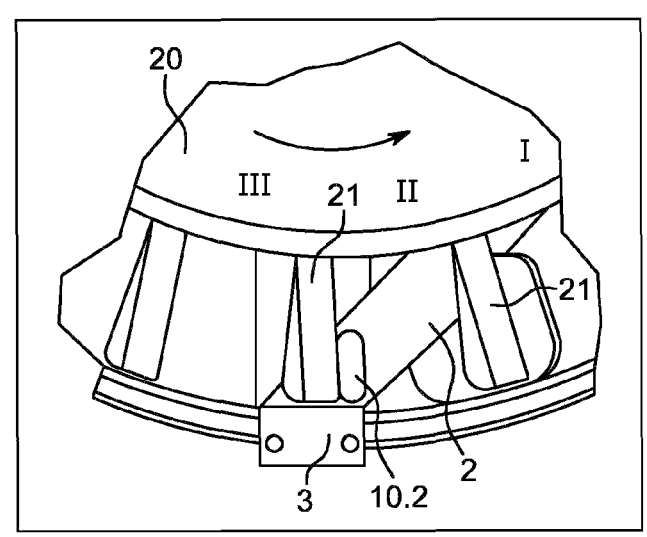
FIG. 3.9

DEVICE AND METHOD FOR TESTING TABLETS

CROSS-REFERENCES TO RELATED APPLICATIONS

This application is the U.S. National Stage of International Application No. PCT/EP2016/070229, filed Aug, 26, 2016, which designated the United States and has been published as International Publication No. WO 2017/036980 A1 and which claims the priority of German Patent Application, Serial No. 10 2015 114 600.2, filed Sep. 1, 2015, pursuant to 35 U.S.C. 119(a)-(d).

BACKGROUND OF THE INVENTION.

The subject matter of the present invention is a device and a method for testing tablets. The device for testing tablets includes a test chamber, which has a crusher jaw and a counter-jaw opposite the crusher jaw. The device has a movable sheet metal strip, which is configured to position a tablet for testing. The longitudinal axis of the movable sheet metal strip is aligned at an angle of less than 90° relative to the longitudinal axis of the direction of movement of the crusher jaw and the direction of movement of the sheet metal strip corresponds to the longitudinal axis of the sheet metal strip.

As part of the quality control of tablets, it is necessary to check their properties such as length, width, breaking strength and weight. The German Pharmacopoeia contains the relevant legal provisions. If possible, this process should be performed automatically, so that a large number of tablets can be checked within a short time. In addition, it must be ensured that tablets of different shapes and sizes can be positioned correctly to allow error-free measurement. Several devices and methods are known in the prior art that are suitable for this purpose.

German Patent DE 197 33 436 C2 describes a tablet testing device for testing oblong tablets. Here, the tablets to be tested are first conveyed by a feeder to a balance and then from the balance onto a transport device. The tablets are hereby placed on the transport device in a defined position so that further tests can take place. The correct orientation of the tablet when placed on the transport device is accomplished in that the balance bowl has a bottom in the form of a groove. The bottom ensures that the oblong tablets are appropriately aligned. In addition, a stumbling block, for example a wedge, may be located on the transport device, which is provided for the case that the tablet falls onto the transport device with its head side. In this case, the stumble block causes the tablet to tilt to its long side. According to this invention, a correct orientation of a tablet is effected, however, upon its transfer through the groove the tablet is exposed to considerable forces that may damage the tablet.

German Patent DE 10 2006 004 215 B4 discloses a break strength tester for tablets of different shapes and sizes. In order to align the tablets, two counter-rotating, juxtaposed centering rollers are used here. When an oblong tablet is placed on the rollers, their rotation causes the oblong tablet to become oriented longitudinally between the rollers. Subsequently, the strength can be tested by a crusher jaw. In order to enable alignment of tablets of different shapes and sizes, the device is equipped with a pivoting positioner, which can align the rollers differently. The alignment is fast, but the use of rollers after a break test makes the device difficult to clean.

The utility model application DE 298 24 199 U1 discloses a system for carrying out hardness tests on specimens, using an alternative approach. In this case, the tablet is placed on a test bench, but then no alignment of the tablet is performed. Instead, the alignment of the specimen is determined by a device for detecting the position. Then, a pressure piston and an abutment, which are used for the hardness test of the tablet, are aligned accordingly, so that the tablet can be tested. However, this invention requires a complicated and expensive construction, which must include means for image recognition.

PCT publication WO 2013/061223 A2 discloses a method and a device for testing tablets, which aligns the tablets with the aid of a pivotable rocker. The tablet is hereby placed on the initially horizontal rocker, which then performs a pivot movement. As a result of gravity and the pivot movement the tablet aligns with a positioning surface. The positioning surface in this case has a concave shape, which runs along the shape defined by the movement of the rocker. In addition, to assist in the correct orientation of the tablet, the pivotable rocker may be inclined at an angle relative to the positioning surface, or may have an additional device on the side opposite the positioning surface, which performs a pre-alignment of the tablet. After positioning and return of the rocker to a horizontal position, the tablet is tested. Since in this case the positioning is done under the influence of gravity and the rocking motion must be carried out at a sufficient speed, it cannot be ruled out that excessive forces may act on the tablet during orientation.

SUMMARY OF THE INVENTION

The object of the present invention was therefore to provide a device and a method for testing tablets, which aligns the tablet prior to being tested in a gentle, fast and easy-to-implement way, and also ensures easy cleaning.

The object is achieved by a device according to the corresponding independent device claim and a method according to the independent method claim. The device for testing tablets includes a test chamber, which has a crushing jaw and a counter-jaw opposite the crushing jaw. The device has a movable sheet metal strip, which is configured to position a tablet for testing. The longitudinal axis of the movable sheet metal strip is aligned at an angle of less than 90° relative to the longitudinal axis of the direction of movement of the breaking jaw and the direction of movement of the sheet metal strip corresponds to the longitudinal axis of the sheet metal strip.

In the test chamber, an abutment is preferably provided which delimits the test chamber and extends from the counter-jaw in the direction of the crusher jaw, wherein the abutment is arranged substantially at a right angle relative to the counter-jaw. In a particularly preferred embodiment, the abutment is designed as a part of a driver. The driver is preferably a transport star.

The tablet is preferably an oblong tablet, which, due to its shape, aligns with its length on the corresponding positioning surface (counter-jaw or abutment). However, it is also possible to position tablets of other shapes, such as round tablets. In this case, the process merely leads to the tablet being moved to the positioning surface, so that a test can be carried out. The test itself does not involve human input. Preferably, the device has a computer that not only controls the movements but also stores the measured values.

In a further advantageous embodiment, the tablet is positionable along the abutment by movement of the sheet metal strip in one direction. In addition, the tablet can be positioned along the counter-jaw by moving the sheet metal strip in the opposite direction.

According to the invention it is further preferred when a part of the sheet metal strip forms a bottom of the test chamber. When the driver carries the tablet into the test chamber, the tablet automatically comes to lie on the sheet metal strip and can be aligned accordingly for the further testing steps.

In order to enable a better positioning of the tablet along the positioning surfaces, the positioning surfaces (counter-jaw and abutment) may have a special shape. According to the invention, a planar shape is considered to be particularly advantageous. However, it is also possible to design the positioning surfaces in a concave shape. It is also possible to provide the positioning surfaces with a roughened surface or a special pattern, which allows better alignment of the tablets.

In a particularly preferred embodiment of the present invention, the crusher jaw is adapted to measure the diameter of the tablet, which is aligned along the counter-jaw or the abutment, wherein the diameter is measured in the direction of movement of the crusher jaw. When the tablet is an oblong tablet, first the width of the tablet is measured and then, in a second position, the length of the tablet.

Preferably, the crusher jaw is further adapted to test the breaking hardness of the tablet, which is aligned along the counter-jaw or the abutment.

In a further advantageous embodiment of the invention, the angle between the longitudinal axis of the movable sheet metal strip and the longitudinal axis of the direction of movement of the crusher jaw is between 20° and 60°, preferably between 40° and 50°. The angle is chosen so that the tablet to be tested can be aligned quickly when moving the sheet metal strip along the counter-jaw and along the abutment.

In a particularly preferred embodiment, an adjusting device is provided, on which the sheet metal strip is arranged, wherein the angle between the longitudinal axis of the movable sheet-metal strip and the longitudinal axis of the direction of movement of the crusher jaw is adjustable by means of the adjusting device. Thus, the angle between the longitudinal axis of the movable sheet metal strip and the longitudinal axis of the direction of movement of the crusher jaw can be adapted to certain shapes of tablets or different sized tablets. This allows a precise alignment of different tablets.

In addition, according to the invention it is preferred when a driver is provided, which pushes the tablet material out of the test chamber after the test. The driver can thus transport the tablet into the test chamber, and also push the tablet or tablet fragments out of the test chamber after the test. It is inventively preferred when the abutment is a part of the driver.

The invention also includes a method for testing tablets according to claim 10. In the method according to the invention, a tablet, preferably an oblong tablet, is placed on a movable sheet metal strip for testing and the tablet is aligned along at least one positioning surface by movement of the sheet metal strip and then at least one parameter of the tablet is measured.

The tablet is oriented by coming into contact with a positioning surface as a result of the diagonal movement of the sheet metal strip and is aligned at this positioning surface along its longitudinal axis due to the movement of the sheet metal strip. Subsequently, the at least one parameter of the tablet is tested.

Preferably, in order to test the tablet in a first position, the tablet is positioned by moving the movable sheet metal strip in a first direction so that the tablet is aligned along a counter-jaw. To perform a further test, the tablet is positioned in a further position for testing by moving the movable sheet metal strip in the opposite direction so that the tablet contacts the abutment and is aligned along the abutment. When the tablet is an oblong tablet, the width of the tablet is first measured in a first position and then the length of the tablet is measured in a second position. After the length measurement, the break test is performed in the same position.

The method according to the invention is preferably carried out as follows:

1. A tablet, preferably an oblong tablet, is moved onto the sheet metal strip.
2. The tablet is aligned by movement of the sheet metal strip in one direction on a first positioning surface (counter jaw).
3. The width of the tablet is examined.
4. The tablet is aligned by the movement of the sheet metal strip in the opposite direction of movement at another positioning surface (abutment).
5. The length of the tablet is examined.
6. A beak test of the tablet is performed.
7. The remnants of the tablet are removed from the test chamber.

Depending on the desired test objectives, a different alternative sequence of the method is possible: for example, a variant in which only the diameter is measured, but no crush test is performed, or only a crush test is performed without prior measurement of the diameter. For the purposes of the present invention, the term diameter measurement encompasses a width and/or length measurement of the tablet.

According to the invention, the test of the tablet is carried out by a crusher jaw. The crusher jaw moves in the direction of the counter-jaw and is driven by a motor. The crusher jaw is designed to test the diameter of the tablet and its breaking strength. The dimensions are measured in that the crusher jaw is moved in the direction of the counter-jaw until a defined counterforce occurs. This counterforce indicates that the crusher jaw has contacted the tablet. The path traversed by the crusher jaw is stored, and optionally the diameter of the tablet is calculated directly from the traversed path. The diameter of the tablet is calculated from the maximum traversable distance between the starting position of the crusher jaw and the abutment minus the actually traversed path of the crusher jaw.

The diameter can be measured either after the tablet has been positioned along the counter-jaw or after the tablet has been aligned along the abutment. When a positioning along the counter-jaw was performed, then the crusher jaw measures the width diameter. When a positioning along the abutment was performed, the crusher jaw measures the longitudinal diameter of the tablet.

Preferably, the crusher jaw is also adapted to measure the breaking hardness of the tablet. For this purpose, the crusher jaw is moved in the direction of the counter-jaw until a defined counterforce acts on the crusher jaw. This indicates that the crusher jaw has reached the tablet. Then the force exerted by the crusher jaw is increased until the tablet breaks. The force applied by the crusher jaw, which was necessary to cause breakage of the tablet, is stored by the integrated computing system of the device. The breaking hardness can only be measured if the tablet has been previously aligned with a positioning surface. If the alignment was performed on the counter-jaw, the breaking hardness is tested with respect to the short side (width) of the tablet. If the alignment was performed on the abutment, the breaking hardness is tested with respect to the long side (length) of the tablet.

In a further embodiment, the tablet or its remnants are pushed by a driver out of the test chamber after the test. In an advantageous variant of the invention, the driver performs a movement in the direction of the abutment. This movement is supported by engine power. Again, the process is controlled by the processing unit integrated in the testing device. In a particularly preferred embodiment the driver itself forms the abutment.

The device according to the invention and the method according to the invention are explained in more detail below with reference to FIGS. 1 to 3, wherein

DETAILED DESCRIPTION OF PREFERRED EMBODIMENTS

Figure 1:
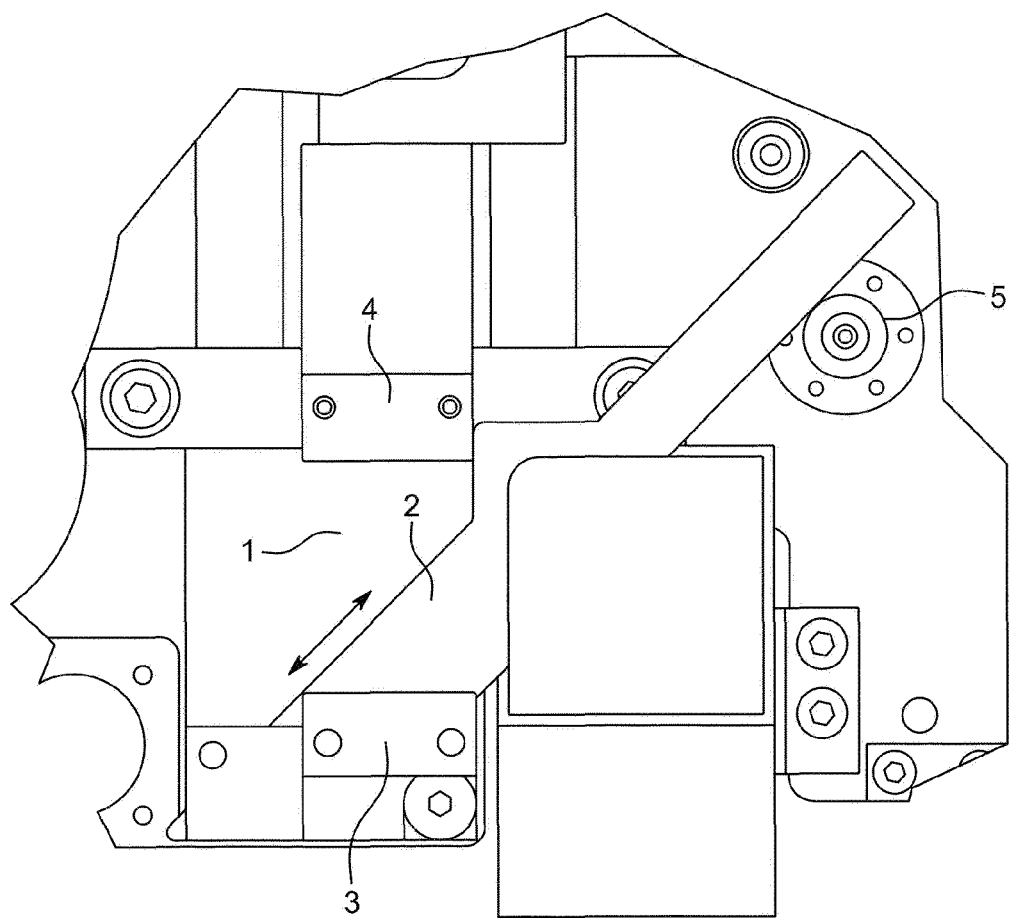
FIG. 1 shows a plan view of a test chamber according to the invention without cover (driver)
Figure 2:
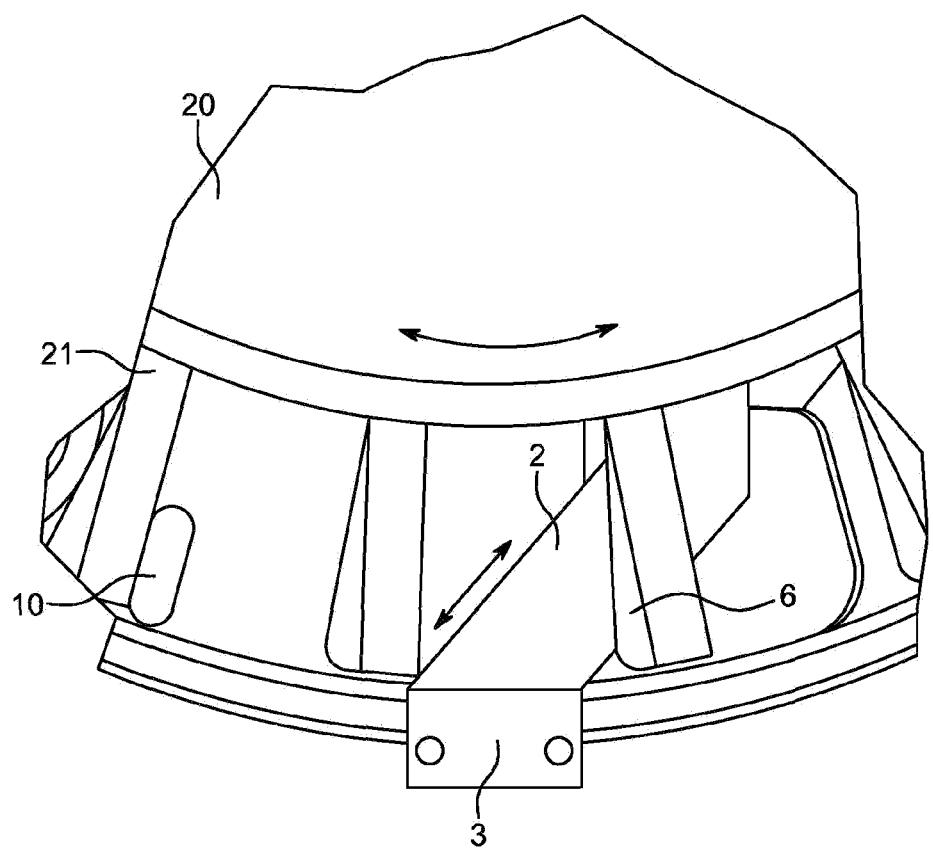
FIG. 2 shows a plan view of a device according to the invention with an oblong tablet to be tested, and FIGS. 3.1 to 3.9 show a possible sequence of the individual method steps of the method according to the invention for testing an oblong tablet.

As shown in FIGS. 1 and 2, the device according to the invention includes a test chamber (1), which includes a crusher jaw (4) and a counter-jaw (3) opposite the crusher jaw. The device has a movable sheet metal strip (2), configured to position a tablet for testing. The longitudinal axis of the movable sheet metal strip (2) is aligned at an angle of less than 90° relative to the longitudinal axis of the direction of movement of the crusher jaw (4) and the direction of movement of the sheet metal strip (2) corresponds to the longitudinal axis of the sheet metal strip (2). The direction of movement of the sheet metal strip (2) is indicated by a double arrow and is oriented in the present case at an angle of approximately 45° relative to the longitudinal axis of the direction of movement of the crusher jaw (4). In the illustrated embodiment, the direction of movement of the crusher jaw (4) is perpendicular in the direction of the counter-jaw (3). In the present embodiment the movement of the sheet metal strip is accomplished via a threaded spindle (5). As a result, the length of the travel path can be adapted individually to each oblong.

In the method according to the invention, a tablet (10), preferably an oblong tablet, is moved into the test chamber (1). As a result of the movement of the metal strip (2) in a first direction the tablet comes in contact with a first positioning surface, namely the counter-jaw (3), and is aligned therewith. The tablet (10) is oriented by being brought in contact with the counter jaw (3) by the movement of the sheet metal strip (2) and by being aligned on the counter-jaw (3) along its longitudinal axis due to the movement of the sheet-metal strip (2). Subsequently, at least one parameter of the tablet (10) is measured. In order to carry out a further test, the tablet (10) is positioned for testing in a further position by moving the metal strip (2) in a direction opposite the first direction of movement, so that the tablet (10) is aligned along another positioning surface of the abutment (6).

In a preferred embodiment of the device shown in FIG. 2, a driver (20) is provided which pushes the tablet material out of the test chamber after the test. In the present embodiment, the driver (20), operating on the principle of a rotary feeder, includes a rotatably mounted round body and a plurality of driver arms (21) extending radially therefrom. At the transition to the base body, the distance between the driver arms (21) corresponds substantially to the width of the crusher jaw (4) (see also FIGS. 3.5, 3.7 and 3.8) and in the test position of the driver (20) the lateral boundaries of the test chamber (1) are each formed by two adjacent driver arms (21). Due to the radial arrangement of the driver arms (21), this does not result in a rectangular test chamber (1), but a trapezoidal test chamber. In the context of the present application, a testing position of the driver is defined in that the crusher jaw (4), the counter-jaw (3) and two of the arms of the driver (21) are aligned substantially trapezoidal with respect to each other thus enabling movement of the crusher jaw (4) between the two arms of the driver (21).

The driver (20) can also push the tablet (10) onto the sheet metal strip (2) into the test chamber prior to the testing. The driver (20) can thus transport the tablet (10) onto the sheet metal strip (2) and, after the test, push the tablet (10) or tablet remnants off the sheet-metal strip (2) out of the test chamber (1). The direction of movement of the driver is indicated with a curved double arrow.

In the present case, the abutment (6) is constructed as a part of the driver (20). For this purpose, an abutment (6) is respectively attached to the driver arms (21) on the side facing away from the direction of rotation when inserting the tablets (10) into the test chamber (1), wherein the angle between the abutment (6) and the driver arms (21) is designed so that in the testing position of the driver (20) the abutment (6) is substantially at a right angle relative to the counter-jaw (3). In FIG. 2, a counterclockwise direction of rotation is provided to transport the tablet (10) into the test chamber (1). Accordingly, in FIG. 2 the abutments (6) are arranged respectively on the left side of the driver arms (21).

FIGS. 3.1 to 3.9 show a possible sequence for the inventive method for testing tablets for use in a semi-automatic device for testing tablets. Roman numerals I to III designate the individual positions in the driver.

As shown in FIG. 3.1, the tablet to be tested (10.1), in the present case an oblong tablet (10.1), is manually positioned by the user on the arm (21) of the driver (20) in a chamber as close as possible to the outer radius of the driver (position I). Before the oblong specimen (10.1) is conveyed to the sheet metal strip for testing in the test chamber, the sheet metal strip (2) moves to the uppermost position, wherein the direction of movement of the sheet metal strip (2) is indicated by the arrow. After rotation of the driver (20) by one position (direction of movement is indicated in FIG. 3.2 by a curved arrow), the oblong specimen (10.1) is moved on the metal strip (2) into the test chamber. The driver (20) is rotated until the, with respect to the direction of rotation, frontal side (i.e., in FIG. 3.2 the right side) of the driver arm (21), which pushes the tablet (10.1), ends flush with the, with respect to the direction of rotation, frontal side of the test chamber (1) (i.e., in FIG. 3.2 also the right side of the test chamber), so that at least a portion of the tablet is located outside the test chamber. At the same time, another tablet (10.2) to be tested can be positioned in the next chamber of the driver (position II).

Thereafter, the driver (20) moves back in the opposite direction (the direction of movement is represented by the curved arrow), as illustrated in FIG. 3.3. The driver (20) is rotated until the tablet (10.1) again comes to lie completely within the test chamber. This has the purpose to clear the way for the crusher jaw (4) and as a result the tablet (10.1) rests against the abutment (6) and optionally also against the counter-jaw (3). In this position the abutment (6) is then also oriented at a right angle relative to the counter-jaw (3) and the crusher jaw (4) and forms a left-sided open rectangle with the latter, i.e., it adjoins directly to their right edges.

FIG. 3.4 shows that the tablet (10.1) is aligned on the counter-jaw (3) along its longitudinal axis as a result of the movement of the sheet metal strip (2). The direction of movement of the sheet metal strip (2) obliquely downward in the direction of the counter-jaw (3) is indicated by an arrow. Due to the arrangement of the longitudinal axis of the movable sheet-metal strip (2) at an angle of less than 90° relative to the longitudinal axis of the direction of movement of the crusher-jaw, in the present embodiment about 45°, the oblong specimen (10.1) can be aligned at the counter-jaw (3). If the oblong specimen (10.1) does not yet contact the counter-jaw before the metal strip (2) starts to move, the oblong specimen (10.1) contacts the counter-jaw after having been moved against the counter-jaw by movement of the sheet metal strip (2).

In a next step, illustrated in FIG. 3.5, the crusher jaw (4) moves in the direction of the counter-jaw (3) between the two arms of the driver (21) to obtain a parameter of the oblong specimen (FIG. 10.1). In the present embodiment, first the width of the oblong specimen (10.1) is determined. After measuring the width of the oblong specimen (10.1), the crusher jaw moves back to its original position.

In order to determine a further parameter, the sheet metal strip (2) moves in the opposite direction in the subsequent step, as shown in FIG. 3.6. The direction of movement of the sheet metal strip (2) obliquely upward in the direction of the abutment (6) is indicated by an arrow. By moving the sheet metal strip (2) in the opposite direction, the oblong specimen (10.1) is moved in the direction of the abutment (6) and contacts this positioning surface. Due to the oblique arrangement of the sheet metal strip (2), the movement of the sheet metal strip (2) causes the oblong specimen (10.1) to align lengthwise with the abutment (6), so that the oblong specimen (10.1) comes to rest rotated by 90° relative to its first position. The abutment (6) is constructed as a part of the driver (20).

In the following step, the crusher jaw (4) moves back in the direction of the counter-jaw (3) to determine the length of the oblong specimen (10.1). This is shown in FIG. 3.7. After measuring the length of the oblong specimen (10.1), the breaking hardness is determined. For this purpose, the crusher jaw (4) exerts a force in the direction of the counter-jaw (3) until the oblong specimen (10.1) breaks between the crusher jaw (4) and the counter-jaw (3), as can be seen in FIG. 3.8. Further movement of the driver (20) disposes of the broken oblong specimen. This is shown in FIG. 3.9. The direction of rotation of the driver (20) is represented by the curved arrow. After disposing of the broken oblong specimen, position I of the carrier is cleared and the oblong specimen is transported from position II (10.2) on the sheet metal strip (2) into the test chamber for being measured. In position III, another oblong specimen can then be positioned, which can be tested in a subsequent step.

LIST OF REFERENCE NUMERALS 1 test chamber
2 movable sheet metal strips
3 counter-jaw
4 crusher jaw
5 drive
6 abutment
10 tablet/oblong specimen
10.1 oblong specimen in position I during the inspection process
10.2 2. oblong specimen in position II
20 driver
21 arms of the driver

What is claimed is:

1. A device for testing tablets, comprising
a test chamber having a crusher jaw and a counter jaw opposite the crusher jaw;
a driver comprising a round base body and a plurality of driver arms extending radially from the round base body, wherein a distance between the driver arms at a transition of the driver arms to the base body corresponds substantially to a width of the crusher jaw,
wherein in a testing position of the driver for testing a tablet in the test chamber two adjacent ones of the driver arms form lateral boundaries of the test chamber,
wherein via rotation of the driver a first one of the driver arms pushes a tablet to be tested into the test chamber, and a second one of the driver arms adjacent the first driver arm pushes tablet material out of the test chamber after testing of the tablet; and
a movable sheet metal strip, adapted to position the tablet for testing, wherein an angle between a longitudinal axis of the movable sheet metal strip and a longitudinal axis of a direction of movement of the crusher jaw is less than 90°, and a direction of movement of the sheet-metal strip corresponds to the longitudinal axis of the sheet-metal strip,
said device being adapted so that the driver rotates in a first direction of rotation from the tablet to the test chamber until a side of the driver facing in the direction of rotation ends flush with a side of the test chamber facing in the direction of rotation so that at least a portion of the tablet is located outside the test chamber, and after rotation in the first direction of rotation the driver rotates in a second direction of rotation opposite the first direction of rotation until the tablet is located completely within the test chamber again.

2. The device of claim 1, further comprising an abutment provided in the test chamber and arranged substantially at a right angle relative to the counter-jaw, said abutment delimiting the test chamber and extending from the counter-jaw in a direction of the crusher jaw.

3. The device of claim 1, wherein the tablet is positionable along the abutment by movement of the sheet metal strip in a first direction and/or the tablet is positionable along the counter jaw in a second direction opposite the first direction.

4. The device of claim 1, wherein a portion of the sheet metal strip forms a bottom of the test chamber.

5. The device of claim 1, wherein the crusher jaw is adapted to measure a diameter of the tablet in a direction of movement of the crusher jaw when the tablet is aligned along the counter-jaw or the abutment.

6. The device of claim 1, wherein the crusher jaw is adapted to test a breaking hardness of the tablet, when the tablet is aligned along the counter-jaw or the abutment.

7. The device of claim 1, wherein the angle between the longitudinal axis of the movable sheet metal strip and the longitudinal axis of the direction of movement of the crusher jaw is between 20° and 60°.

8. The device of claim 7, wherein the angle between the longitudinal axis of the movable sheet metal strip and the longitudinal axis of the direction of movement of the crusher jaw is between 40° and 50°.

9. The device of claim 1, further comprising an adjusting device, said sheet-metal strip being arranged on the adjusting device, said adjusting device being adapted for adjusting the angle between the longitudinal axis of the movable sheet metal strip and the longitudinal axis of the direction of movement of the crusher-jaw.

10. The device of claim 1, further comprising an abutment arranged on each of the driver arms on a side of the driver arms which faces away from a direction of rotation of the driver during pushing of the tablets into the test chamber, wherein an angle between the abutment and the driver arm is configured so that in the testing position of the driver the abutment is arranged substantially at a right angle relative the counter jaw.

11. A method for testing tablets, comprising:
rotating a driver having driver arms so that one of the driver arms moves a tablet into a test chamber and another one of the driver arms adjacent the one of the driver arms moves tablet material present in the test chamber out of the test chamber,
wherein the driver is rotated in a direction of rotation from the tablet toward the test chamber until a side of the one of the driver arms facing in the direction of rotation ends flush with a side of the test chamber facing in the direction of rotation so that at least a portion of the tablet is located outside the test chamber,
wherein subsequent to rotating the driver in the first direction of rotation the driver is rotated in a second direction of rotation opposite the first direction of rotation until the tablet is located completely within the test chamber again;
placing the tablet on a movable sheet metal strip for testing;
orienting the tablet along at least one positioning surface by movement of the sheet metal strip; and
measuring at least one parameter of the tablet.

12. The device of claim 11, wherein for testing the tablet in a first position the tablet is positioned by moving the movable sheet metal strip in a first direction so that the tablet is oriented along a counter-jaw and/or the tablet is positioned for testing in a further position by moving the movable sheet metal strip in a direction opposite the first direction, so that the tablet is oriented along an abutment.

13. The method of claim 12, wherein the testing of the tablet is performed by a crusher jaw which performs a movement in the direction of a counter jaw.

14. The method of claim 13, wherein the testing comprises testing of a diameter of the tablet aligned along the at least one positioning surface, wherein for the testing of the diameter the crusher jaw moves in the direction of the counter jaw until a force having a predefined value acts on the crusher jaw.

15. The method of claim 13, wherein the testing comprises testing of a breaking hardness of the tablet aligned along the at least one positioning surface, wherein for the testing of the breaking hardness the crusher jaw moves in the direction of the counter-jaw until a counter force having a predefined value acts on the crusher jaw, and after the counter force having the predefined value acts on the crusher jaw, a force applied by the crusher jaw is increased in the direction of movement until the tablet breaks.

16. The method of claim 13, wherein the driver arms are each provided with an abutment on the side which faces away from the direction of rotation during insertion of the tablet into the test chamber, and wherein the driver is rotated in the second direction of rotation until the abutment is at substantially at a right angle relative to the crusher jaw and the counter jaw, and the abutment substantially forms an open rectangle with the crusher jaw and the counter jaw.

* * * * *